United States Patent
Franci (10) Patent No.: US 10,584,078 B2
(45) Date of Patent: Mar. 10, 2020

(54) DUAL RUN CASSETTE FOR THE SYNTHESIS OF 18F-LABELLED COMPOUNDS

(71) Applicant: GE Healthcare Limited, Buckinghamshire (GB)

(72) Inventor: Xavier Franci, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 504 days.

(21) Appl. No.: 15/033,321

(22) PCT Filed: Nov. 12, 2014

(86) PCT No.: PCT/EP2014/074330
§ 371 (c)(1),
(2) Date: Apr. 29, 2016

(87) PCT Pub. No.: WO2015/071288
PCT Pub. Date: May 21, 2015

(65) Prior Publication Data
US 2016/0257622 A1 Sep. 8, 2016

Related U.S. Application Data

(60) Provisional application No. 61/903,486, filed on Nov. 13, 2013.

(51) Int. Cl.
*C07B 59/00* (2006.01)
*A61K 51/04* (2006.01)
*B01J 19/00* (2006.01)

(52) U.S. Cl.
CPC ........ *C07B 59/005* (2013.01); *A61K 51/0491* (2013.01); *B01J 19/0046* (2013.01);
(Continued)

(58) Field of Classification Search
CPC ....... B01L 19/08; B01L 19/081; B01J 19/004; B01J 2219/00927; C07B 59/00; C07B 59/002; C07B 59/005; C07B 2200/05
See application file for complete search history.

(56) References Cited

U.S. PATENT DOCUMENTS 5,082,980 A * 1/1992 Berridge ............... C07B 59/001
376/201
7,413,714 B1  8/2008 Schwalbe et al.
(Continued)

FOREIGN PATENT DOCUMENTS

JP  2007-319254 A  12/2007
WO  WO 2012/089594 A1  7/2012
(Continued)

OTHER PUBLICATIONS

Chinese Application and Search Report in corresponding Chinese Appl. No. 201410858370.9 dated May 13, 2016. (English Translation attached).
(Continued)

*Primary Examiner* — Jill A Warden
*Assistant Examiner* — Dwayne K Handy
(74) *Attorney, Agent, or Firm* — Arent Fox, LLP (57) ABSTRACT

The invention provides a new chemical process, a new cassette configuration, and new software. The invention allows one synthesizer in one hot cell to produce sequentially two batches of [$^{18}$F]-labelled PET tracer in the same day.

14 Claims, 4 Drawing Sheets

(52) U.S. Cl.
CPC ..... *C07B 59/00* (2013.01); *B01J 2219/00495* (2013.01); *B01J 2219/00716* (2013.01); *B01J 2219/00731* (2013.01)

(56) References Cited

U.S. PATENT DOCUMENTS

| | | |
|---|---|---|
| 2011/0305618 A1* | 12/2011 | Graham ................. A61K 51/04 |
| | | 423/249 |
| 2012/0108858 A1 | 5/2012 | Kiselev |
| 2012/0283490 A1 | 11/2012 | Gangadharmath et al. |
| 2013/0060017 A1 | 3/2013 | Eshima et al. |
| 2013/0144052 A1 | 6/2013 | Mueller |

FOREIGN PATENT DOCUMENTS

| | | |
|---|---|---|
| WO | 2013/053940 A1 | 4/2013 |
| WO | 2013/053941 A1 | 4/2013 |

OTHER PUBLICATIONS

International Search Report and Written Opinion regarding International Application No. PCT/EP2014/074330, dated Jan. 29, 2015, 11 pages.

\* cited by examiner

DUAL RUN CASSETTE FOR THE SYNTHESIS OF 18F-LABELLED COMPOUNDS

CROSS-REFERENCE TO RELATED APPLICATIONS

This application is a filing under 35 U.S.C. 371 of international application number PCT/EP2014/074330, filed Nov. 12, 2014, which claims priority to U.S. application No. 61/903,486, filed Nov. 13, 2013, the entire disclosures of each of which are hereby incorporated by reference.

TECHNICAL FIELD OF THE INVENTION

The present invention concerns devices and methods for the automated synthesis of [$^{18}$F]-labelled compounds, in particular those suitable for use as in vivo imaging agents for positron emission tomography (PET). In particular, the focus of the present invention is for the automated synthesis of more than one batch of an [$^{18}$F]-labelled compound using just one disposable cassette.

DESCRIPTION OF RELATED ART

Radiolabelled compounds for use as in vivo imaging agents are currently typically prepared by means of an automated synthesis apparatus (alternatively "radiosynthesizer"). Such automated synthesis apparatuses are commercially available from a range of suppliers, including: GE Healthcare; CTI Inc.; Ion Beam Applications S.A. (Chemin du Cyclotron 3, B-1348 Louvain-La-Neuve, Belgium); Raytest (Germany) and Bioscan (USA). The radiochemistry takes place in a "cassette" or "cartridge" designed to fit removably and interchangeably onto the apparatus, in such a way that mechanical movement of moving parts of the apparatus controls the operation of the cassette. Suitable cassettes may be provided as a kit of parts that is assembled onto the apparatus in a number of steps, or may be provided as a single piece that is attached in a single step, thereby reducing the risk of human error. The single piece arrangement is generally a disposable single use cassette which comprises all the reagents, reaction vessels and apparatus necessary to carry out the preparation of a given batch of radiopharmaceutical.

Figure 1:
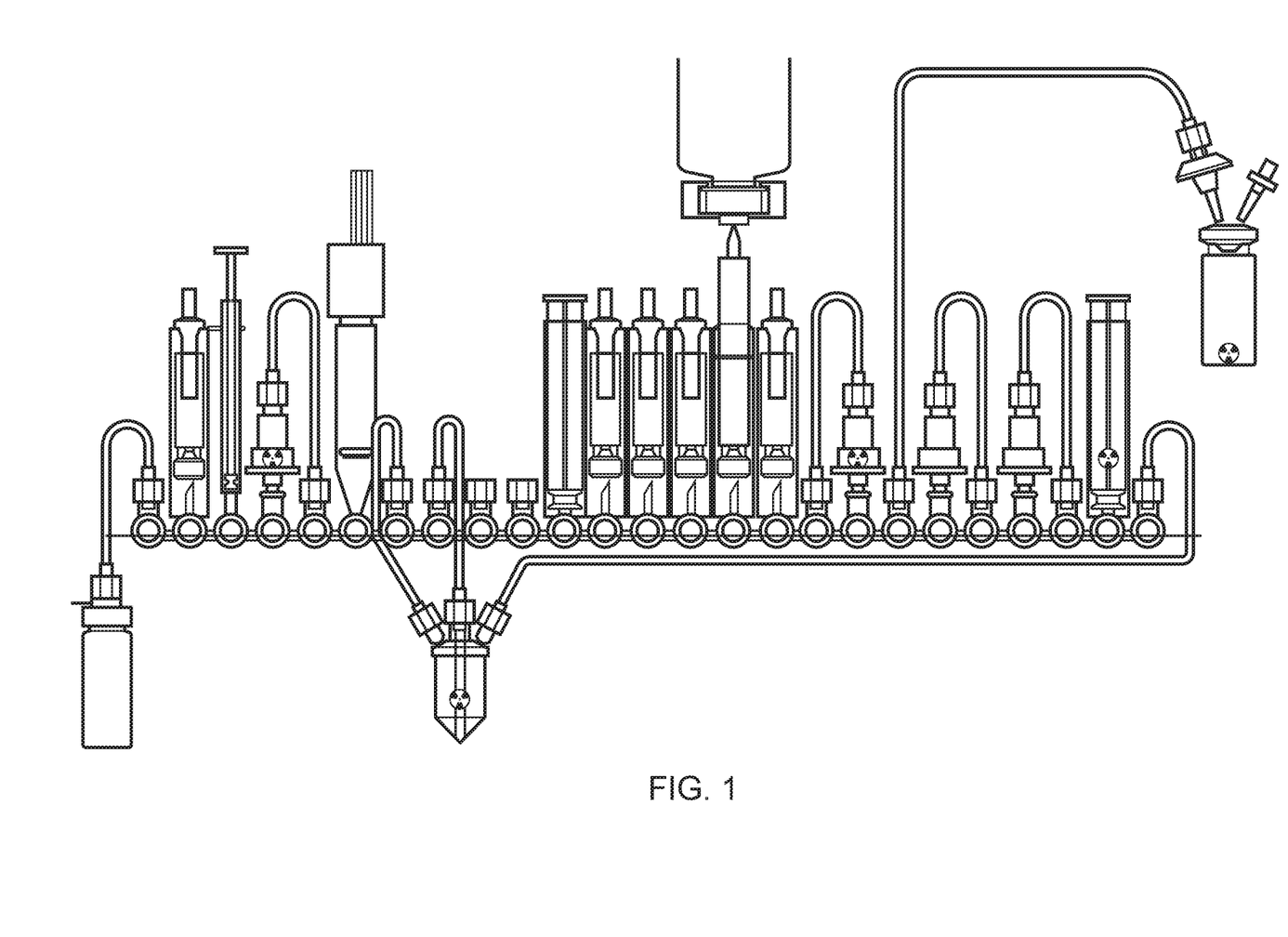
FIG. 1 and FIG. 2 illustrate examples of known cassettes for the production of one batch per cassette of an [$^{18}$F]-labelled compound.
Figure 2:
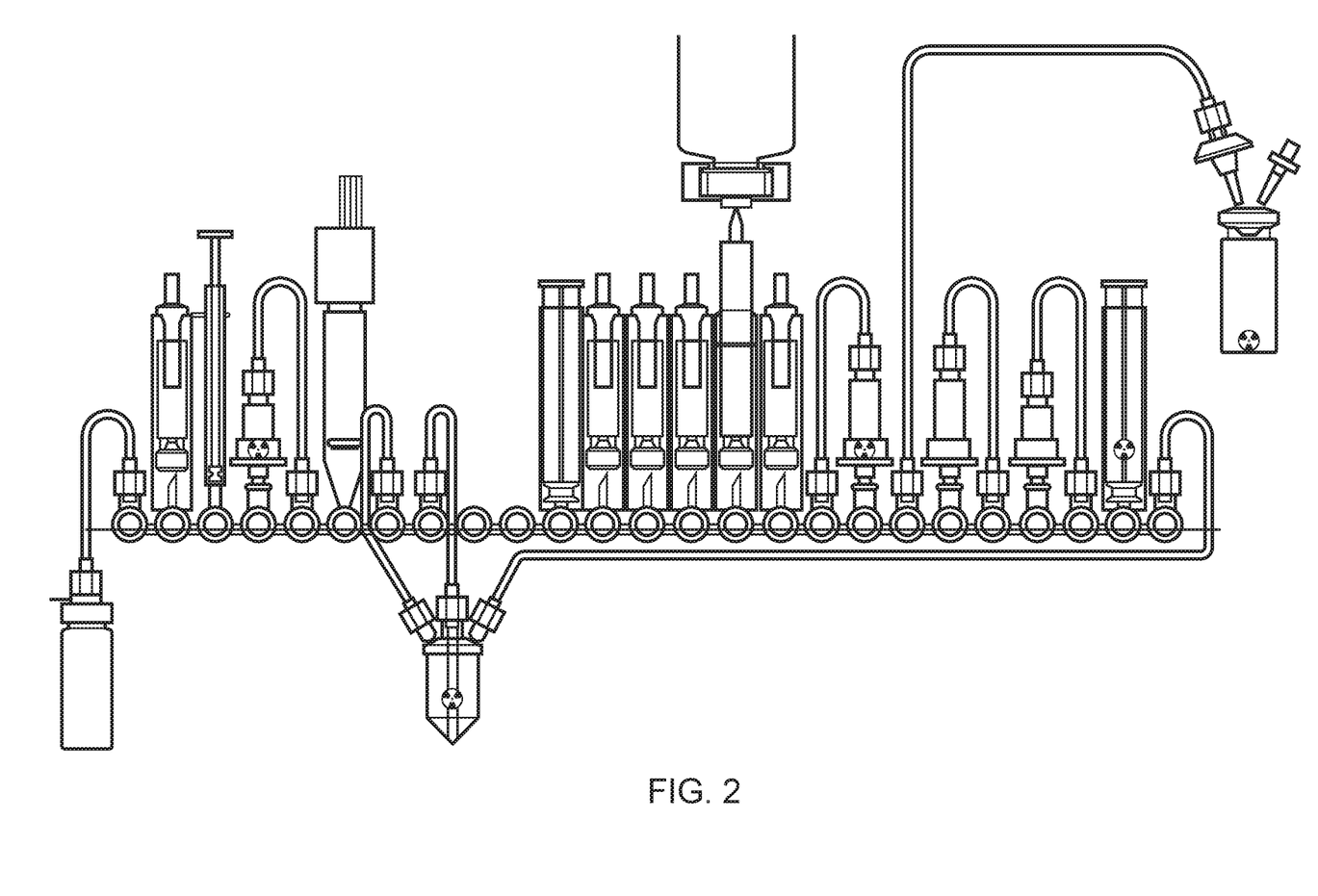

The commercially-available GE Healthcare FASTlab™ cassette is an example of a disposable single piece type of cassette pre-loaded with reagents comprising a linear array of valves, each linked to a port where reagents or vials can be attached. Each valve has a male-female joint which interfaces with a corresponding moving arm of the automated synthesis apparatus. External rotation of the arm thus controls the opening or closing of the valve when the cassette is attached to the apparatus. Additional moving parts of the apparatus are designed to clip onto syringe plunger tips, and thus raise or depress syringe barrels. The FASTlab™ cassette has 25 identical 3-way valves in a linear array, examples of which are shown in FIGS. 1 and 2. FIG. 1 illustrates the commercially-available FDG Phosphate FASTlab™ cassette, and FIG. 2 the commercially-available FDG Citrate FASTlab™ cassette.

Synthesis of [$^{18}$F]fluorodeoxyglucose ([$^{18}$F]FDG) on the cassettes of FIGS. 1 and 2 is carried out by nucleophilic fluorination with [$^{18}$F]fluoride produced by a $^{18}$O(p,n)18F$^-$ reaction. The [$^{18}$F]fluoride so-produced enters the cassette at position 6 and travels to a QMA (quaternary methyl ammonium anion exchange) solid phase extraction (SPE) column placed at position 4 via tubing at position 5. The [$^{18}$F] fluoride is retained by an ion-exchange reaction and the $^{18}$O-water is allowed to flow through the common pathway of the cassette to be recovered at position 1. [$^{18}$F]Fluoride retained on the QMA is then eluted with an eluent solution (acetonitrile solution of Kryptofix™ 222 and potassium carbonate at position 2) withdrawn in the syringe at position 3 and into the reaction vessel (connected by three tubings, one leading to each of positions 7, 8 and 25). Water is evaporated and mannose triflate precursor (from position 12) is added to the reaction vessel. Then the [$^{18}$F]-labelled mannose triflate ([$^{18}$F]fluorotetraacetylglucose, FTAG) is trapped and so separated from [$^{18}$F]fluorides on an environmental tC18 SPE column at position 18 via tubing at position 17 to undergo hydrolysis with NaOH (from the vial at position 14) to remove acetyl protecting groups. The resulting hydrolyzed basic solution is then neutralized in the syringe placed at position 24 with phosphoric acid in the case of phosphate configuration (FIG. 1) or hydrochloric acid present in a citrate buffer in the case of citrate configuration (FIG. 2). Potential residual [$^{18}$F]fluoride removal takes place on an alumina SPE column at position 20 via tubing at position 21 and removal of weakly hydrophilic impurities on an HLB SPE column (for the phosphate cassette of FIG. 1) or a tC18 SPE column (for the citrate cassette of FIG. 2) at position 22 via tubing at position 23. The final purified solution of [$^{18}$F]FDG is transferred to a collection vial via long tubing connected at position 19.

2 positions on the FASTlab™ cassette are free in the case of each of the known [$^{18}$F]FDG cassettes illustrated in FIGS. 1 and 2, i.e. positions 9 and 10. Caps are placed on the valves at these positions.

A typical [$^{18}$F]FDG production site produces minimum 2 batches of [$^{18}$F]FDG in a day. However, because of the residual activity on the FASTlab™ cassette, transfer line and the shadow from the waste bottle after completion of a batch, it is impossible for safety reasons to carry out back to back runs of the above-described process on the same apparatus. This, in combination with the relatively large size of the FASTlab™ apparatus, means that in order to produce a second batch of [$^{18}$F]FDG in the same day using this process, it is necessary to have a second apparatus in a second hot cell.

It would be desirable to have a means to produce more than one batch of [$^{18}$F]FDG using the FASTlab™ on the same day and in only one hot cell. For both of the above-described commercially-available FASTlab™ [$^{18}$F]FDG cassettes, 23 of the total 25 positions are used. It is therefore not possible to fit all the duplicate components for a second batch onto the same cassette.

SUMMARY OF THE INVENTION

In one aspect the present invention provides a cassette (1) for the synthesis of a plurality of batches of an [$^{18}$F]-labelled positron-emission tomography (PET) tracer wherein said cassette comprises:
  (i) an anion exchange column (3, 4) for each of said plurality of batches;
  (ii) a reaction vessel (5);
  (iii) a vial (2) containing an aliquot of eluent for each of said plurality of batches;
  (iv) a vial (6) containing an aliquot of a precursor compound for each of said plurality of batches;
  (v) reagent vials (7, 8, 9) wherein each reagent vial contains an aliquot of reagent for each of said plurality of batches;

(vi) optionally, a solid-phase extraction (SPE) column for deprotection (10) and/or one or more SPE columns for purification (11, 12); and, (vii) means for cleaning said reaction vessel and said SPE columns.

In another aspect the present invention provides a method for the synthesis of a plurality of batches of an [$^{18}$F]-labelled PET tracer wherein said method comprises:

(a) trapping a first aliquot of [$^{18}$F]fluoride onto a first anion exchange column (3);

(b) providing a first aliquot of a precursor compound in a reaction vessel (5);

(c) passing a first aliquot of eluent through said first anion exchange column (3) to elute said first aliquot of [$^{18}$F]fluoride into said reaction vessel (5);

(d) heating the reaction vessel (5) for a predetermined time to obtain crude [$^{18}$F]-labelled PET tracer;

(e) optionally deprotecting said crude [$^{18}$F]-labelled PET tracer on a SPE column (10);

(f) optionally purifying said crude [$^{18}$F]-labelled PET tracer on one or more SPE columns (11, 12);

(g) cleaning said reaction vessel (5) and said SPE columns (10, 11, 12);

(h) repeating steps (a)-(g) one or more times, each time using a subsequent aliquot of [$^{18}$F]fluoride, a subsequent anion exchange column (4) and a subsequent aliquot of an [$^{18}$F]FDG precursor compound;

wherein said method is carried out on a single cassette (1).

In another aspect the present invention provides a non-transitory storage medium comprising computer readable program code, wherein execution of the computer readable program code causes a processor to carry out the steps of the method of the invention as defined hereinabove.

The present invention allows one synthesizer in one hot cell to produce sequentially multiple batches of an [$^{18}$F]-labelled PET tracer. It has been demonstrated herein that good yields are achieved for each of two sequential [$^{18}$F] FDG batches as well as good trapping and elution of the incoming activity. Quality control analyses of the two batches described in Example 1 hereinbelow demonstrate that each batch meets the pharmacopeia requirements for [$^{18}$F]FDG.

DETAILED DESCRIPTION OF THE PREFERRED EMBODIMENTS

By the term "cassette" is meant a single-use piece of apparatus designed to fit removably and interchangeably onto an automated synthesis apparatus, in such a way that mechanical movement of moving parts of the synthesizer controls the operation of the cassette from outside the cassette, i.e. externally. The term "single-use" as used in the context of a cassette of the present invention means that the cassette is intended to be used once prior to disposal for the production of a plurality of batches of an [$^{18}$F]-labelled PET tracer. Suitable cassettes comprise a linear array of valves, each linked to a port where reagents or vials can be attached, by either needle puncture of an inverted septum-sealed vial, or by gas-tight, marrying joints. In one embodiment each valve is a 3-way valve. In one embodiment each valve is a stopcock valve comprising a rotatable stopcock. Each valve has a male-female joint which interfaces with a corresponding moving arm of the automated synthesis apparatus. External rotation of the arm thus controls the opening or closing of the valve when the cassette is attached to the automated synthesis apparatus. Additional moving parts of the automated synthesis apparatus are designed to clip onto syringe plunger tips, and thus raise or depress syringe barrels. The cassette is versatile, typically having several positions where reagents can be attached, and several suitable for attachment of syringe vials of reagents or chromatography columns. The cassette always comprises a reaction vessel, generally configured such that 3 or more ports of the cassette are connected thereto to permit transfer of reagents or solvents from various ports on the cassette. Cassettes need to be designed to be suitable for radiopharmaceutical manufacture and are therefore manufactured from materials which are of pharmaceutical grade as well as resistant to radiolysis. In one embodiment of the present invention the single-use cassette is a FASTlab™ cassette, i.e. one which is suitable for use with a FASTlab™ automated synthesis apparatus.

In one embodiment of the present invention the various elements of the cassette are selectively fluidly connected. The term "selectively fluidly connected" means that it is possible to select whether or not fluid can pass to and/or from the feature to another feature of the invention, e.g. by use of a suitable valve. In one embodiment of the invention a suitable valve is a 3-way valve having three ports and means to put any two of the three associated ports in fluid communication with each other while fluidly isolating the third port. In another embodiment of the invention a suitable valve is a stopcock valve comprising a rotatable stopcock. In one embodiment, the components of the cassette are selectively fluidly connected along a common pathway. The term "common pathway" is to be understood to be a fluid pathway to which the other components of the system or of cassette of the present invention are selectively fluidly connected. In one embodiment, the common pathway is a linear fluid pathway. In one embodiment, the common pathway is made from a rigid pharmaceutical grade polymeric material that is resistant to radiation. Non-limiting examples of suitable such materials include polypropylene, polyethylene, polysulfone and Ultem®. In one embodiment, said common pathway is made from polypropylene or polyethylene.

By the term "automated synthesis apparatus" is meant an automated module based on the principle of unit operations as described by Satyamurthy et al (1999 Clin Positr Imag; 2(5): 233-253). The term 'unit operations" means that complex processes are reduced to a series of simple operations or reactions, which can be applied to a range of materials. Such automated synthesis apparatuses are preferred for the method of the present invention especially when a radiopharmaceutical composition is desired. They are commercially available from a range of suppliers (Satyamurthy et al, above), including: GE Healthcare; CTI Inc; Ion Beam Applications S.A. (Chemin du Cyclotron 3, B-1348 Louvain-La-Neuve, Belgium); Raytest (Germany) and Bioscan (USA). Automated synthesis apparatuses are designed to be employed in a suitably configured radioactive work cell, or "hot cell", which provides suitable radiation shielding to protect the operator from potential radiation dose, as well as ventilation to remove chemical and/or radioactive vapours. Using a cassette the automated synthesis apparatus has the flexibility to make a variety of different radiopharmaceuticals with minimal risk of cross-contamination, by simply changing the cassette. This approach also has the advantages of simplified set-up hence reduced risk of operator error, improved GMP (good manufacturing practice) compliance, multi-tracer capability, rapid change between production runs, pre-run automated diagnostic checking of the cassette and reagents, automated barcode cross-check of chemical reagents vs the synthesis to be carried out, reagent traceability, single-use and hence no risk of cross-contamination, tamper and abuse resistance.

The term "plurality" used herein in the context of batches of an [$^{18}$F]-labelled PET tracer is intended to refer to more than one batch, where that more than one batch is synthesised on one single-use cassette. In one aspect the term plurality refers to two batches, i.e. a first batch and a second batch. The terms "first batch" and "second batch" represent two separate consecutive syntheses of [$^{18}$F]-labelled PET tracer produced on the same cassette, the second batch being produced only after production of the first batch has been completed, i.e. the product has been collected in the product collection vial. The term "batch" is used to refer a batch of the final synthesised [$^{18}$F]-labelled PET tracer. It is intended that the plurality of batches can be produced on the same day and without need to open the hot cell in which the cassette and automated synthesiser are present.

An "[$^{18}$F]-labelled PET tracer" is a chemical compound that comprises an $^{18}$F atom and is suitable for use as a PET tracer. Non-limiting examples of [$^{18}$F]-labelled PET tracers include [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F]fluorocyclobutane-1-carboxylic acid ([$^{18}$F]FACBC), [$^{18}$F]flumanezil ([$^{18}$F]FMZ), [$^{18}$F]tyrosine, [$^{18}$F]altanaserine, 4-[$^{18}$F]fluoro-3-iodobenzyl guanidine ([$^{18}$F]FIBG), meta-[$^{18}$F]fluorobenzylguanidine ([$^{18}$F]mFBG) and [$^{18}$F]5-fluorouracil. In one embodiment of the present invention the $^{18}$F-labelled compound is selected from [$^{18}$F]FDG, [$^{18}$F]FMISO, [$^{18}$F]FLT and [$^{18}$F]FACBC. In another embodiment of the present invention the $^{18}$F-labelled compound is [$^{18}$F]FDG.

A "reaction vessel" in the context of the present invention is a container of the cassette of the invention where the reactants and reagents required for the synthesis can be sent and the product(s) removed in an appropriate order. The reaction vessel has an internal volume suitable for containing the reactants and reagents and is made from pharmaceutical grade materials resistant to radiation.

An "aliquot" in the context of the method of the present invention is a sufficient quantity of a particular reagent for use in the synthesis of one batch of a PET tracer.

A "precursor compound" is to be understood herein as a non-radioactive derivative of a radiolabelled compound, designed so that chemical reaction with a convenient chemical form of the detectable label occurs site-specifically in the minimum number of steps (ideally a single step) to give the desired radiolabelled compound. To ensure site-specific labelling a precursor compound may have protecting groups. Such precursor compounds are synthetic and can conveniently be obtained in good chemical purity. A number of precursor compounds are well known to be suitable for the synthesis of [$^{18}$F]-labelled compounds, as taught for example in Chapter 7 of "Handbook of Radiopharmaceuticals: Radiochemistry and Applications" (2003 John Wiley & Sons Ltd., Wench & Redvanly, Eds.).

The term "protecting group" refers to a group which inhibits or suppresses undesirable chemical reactions, but which is designed to be sufficiently reactive that it may be cleaved from the functional group in question to obtain the desired product under mild enough conditions that do not modify the rest of the molecule. Protecting groups and methods for their removal (i.e. "deprotection") are well known to those skilled in the art and are described in 'Protective Groups in Organic Synthesis', Theorodora W. Greene and Peter G. M. Wuts, (Fourth Edition, John Wiley & Sons, 2007).

The term "reagent" used herein is a term intended to refer to solvents and reactants used in the synthesis of a particular [$^{18}$F]-labelled PET tracer. Suitably these are stored in a reagent vial. The term "reagent vial" is taken to mean a vial containing one of the reagents for use in the production of the [$^{18}$F]-labelled PET tracer, sufficient for the production of the desired plurality of batches. The term "sufficient" means a suitable amount of a reagent to ensure that the plurality of batches can be obtained. Generally this amount is a little more than the exact amount required. A typical reagent vial is made from a rigid pharmaceutical grade polymer resistant to radiation. Suitable reagents contained in said reagent vials include ethanol, acetonitrile, deprotecting agents and buffers. In one embodiment said deprotecting agent is selected from HCl, NaOH and $H_3PO_4$. In one embodiment said deprotecting agent is NaOH. In one embodiment said buffer is based on a weak acid, for example selected from citrate, phosphate, acetate and ascorbate. For example where the [$^{18}$F]-labelled compound of the present invention is [$^{18}$F]FDG, the single-use cassette comprises a reagent vial containing ethanol, one containing acetonitrile, another containing NaOH and another containing a buffer based on a weak acid selected from citrate or phosphate.

The term "solid phase extraction (SPE)" refers to the sample preparation process by which compounds in a solution are separated from each other based on their respective affinities for a solid (the "solid phase", or "stationary phase") through which the sample is passed and the solvent (the "mobile phase" or "liquid phase") in which they are dissolved. The result is that a compound of interest is either retained on the solid phase or in the mobile phase. The portion that passes through the solid phase is collected or discarded, depending on whether it contains the compound of interest. If the portion retained on the stationary phase includes the compound of interest, it can then be removed from the stationary phase for collection in an additional step, in which the stationary phase is rinsed with another solution known as an "eluent". For the present invention SPE is suitably carried out using an "SPE column" (also often referred to as an "SPE cartridge"), which is readily available commercially and is typically in the form of a syringe-shaped column packed with solid phase. Most known solid phases are based on silica that has been bonded to a specific functional group, e.g. hydrocarbon chains of variable length (suitable for reverse-phase SPE), quaternary ammonium or amino groups (suitable for anion exchange), and sulfonic acid or carboxyl groups (suitable for cation exchange).

The term "eluting" refers to passing a solution through an SPE column with the aim to release a compound or compounds of interest that has or have been bound to the solid phase.

The term "eluent" used hereinabove in connection with SPE generally is also specifically used in connection with the single-use cassette of the present invention to refer to the eluent used to elute [$^{18}$F]fluoride trapped on the anion exchange column. [$^{18}$F]fluoride suitable for use in the synthesis of an [$^{18}$F]-labelled compound is normally obtained as an aqueous solution from the nuclear reaction $^{18}$O(p,n)$^{18}$F. In order to increase the reactivity of [$^{18}$F]fluoride and to reduce or minimise hydroxylated by-products resulting from the presence of water, water is typically removed from [$^{18}$F]fluoride prior to the reaction, and fluorination reactions are carried out using anhydrous reaction solvents (Aigbirhio et al 1995 J Fluor Chem; 70: 279-87). A further step that is used to improve the reactivity of [$^{18}$F]fluoride for radiofluorination reactions is to add a cationic counterion prior to the removal of water. This cationic counterion is dissolved in an organic-aqueous solution and this solution is used as an eluent for eluting [$^{18}$F]fluoride from an anion exchange column on which the [$^{18}$F]fluoride has been trapped. In one embodiment said organic-aqueous solution is an aqueous solution of acetonitrile or methanol. In one embodiment said organic-aqueous solution is an aqueous solution of acetonitrile. Suitably, the counterion should possess sufficient solubility within the anhydrous reaction solvent to maintain the solubility of the [$^{18}$F]fluoride. Therefore, counterions that are typically used include large but soft metal ions such as rubidium or caesium, potassium complexed with a cryptand such as Kryptofix™ 222, or tetraalkylammonium salts, wherein potassium complexed with a cryptand such as Kryptofix™ 222, or tetraalkylammonium salts are preferred. The term Kryptofix™ 222 (or K222) refers herein to a commercially-available preparation of the compound 4,7,13,16,21,24-Hexaoxa-1,10-diazabicyclo[8.8.8]hexacosane.

An "SPE column for deprotection" in the context of the present invention is an SPE column having a solid phase on which a precursor compound having protecting groups is retained following the [$^{18}$F]-labelling reaction in order to remove the protecting groups and obtain the desired [$^{18}$F]-labelled PET tracer. In one embodiment the SPE column for deprotection is a reversed-phase SPE column as defined herein.

"Reversed-phase SPE" makes use of a nonpolar modified solid phase and a polar mobile phase. Compounds are retained by hydrophobic interactions and eluted using a non-polar elution solvent to disrupt the forces that bind the compound to the solid phase. Non-limiting examples of reversed-phase SPE columns include C18, tC18, C8, CN, Diol, HLB, Porapak, RDX, and NH$_2$ SPE columns. In one embodiment of the present invention the reversed-phase SPE column is a tC18 or a HLB SPE column. In one embodiment, said reverse-phase SPE column is a HLB SPE column. In another embodiment of the present invention the reversed-phase SPE column is a tC18 column. In some embodiments of the present invention the tC18 column is an environmental tC18 column, sometimes referred to as a long tC18 column or a tC18 plus column. In one embodiment the reverse-phase SPE column used for deprotection is an environmental tC18 column.

"Normal-phase SPE" makes use of a polar modified solid phase and a non-polar mobile phase. Compounds are retained by hydrophilic interactions and eluted using a solvent that is more polar than the original mobile phase to disrupt the binding mechanism. Non-limiting examples of normal-phase SPE columns include alumina, diol and silica SPE columns. In one embodiment of the present invention said normal-phase SPE column is an Alumina SPE column.

"Anion exchange SPE" utilises electrostatic attraction of charged group on compound to a charged group on the sorbent's surface and can be used for compounds that are charged in solution. The primary retention mechanism of the compound is based mainly on the electrostatic attraction of the charged functional group on the compound to the charged group that is bonded to the silica surface. A solution having a pH that neutralizes either the compound's functional group or the functional group on the sorbent surface is used to elute the compound of interest. A non-limiting example of an anion exchange SPE column is a quaternary ammonium anion exchange (QMA) SPE column.

The term "means for cleaning" refers to a source of reagent selectively fluidly connected to the component to be cleaned. The selective fluid connection suitably comprises a valve and length of flexible tubing. Suitable reagents for cleaning include ethanol and acetonitrile, aqueous solutions thereof, and water. The term "cleaning" in the context of the present invention refers to the process of passing a suitable amount of one or more reagents through a component to be cleaned in order to render it suitable for use in preparation of a subsequent batch of [$^{18}$F]-labelled PET tracer. In one embodiment said means for cleaning said reaction vessel and said SPE columns comprises a source of water fluidly connected to said reaction vessel and to said SPE columns. A suitable source of water is water for injection. In one embodiment said source of water is a water bag fluidly connected to said cassette. In one embodiment said means for cleaning said reaction vessel and said SPE columns comprises a source of acetonitrile fluidly connected to said SPE column for deprotection. In one embodiment said means for cleaning said reaction vessel and said SPE columns comprises a source of ethanol fluidly connected to said SPE columns for purification. Said sources of reagents are in one embodiment present in vials comprised in the cassette of the invention.

The term "trapping" refers to the process wherein a particular compound or compounds binds to the solid phase of an SPE column.

The term "passing" refers to the act of allowing a reactant, reagent or reaction solution to flow through a particular component by the selective opening of valves.

The term "heating" herein means application of heat in order to promote a particular chemical reaction to take place. In the context of [$^{18}$F]-labelling as envisaged herein heat is suitably a temperature in the region of 100-150° C. for a short duration of around 2-10 minutes.

The term "purifying" or "purification" as used herein may be taken to mean a process to obtain substantially pure [$^{18}$F]-labelled compound. The term "substantially" refers to the complete or nearly complete extent or degree of an action, characteristic, property, state, structure, item, or result. The term "substantially pure" can be taken to mean completely pure [$^{18}$F]-labelled compound, which would be ideal, but also [$^{18}$F]-labelled compound that is sufficiently pure to be suitable for use as a PET tracer. The term "suitable for use as a PET tracer" means that the substantially pure [$^{18}$F]-labelled compound is suitable for intravenous administration to a mammalian subject followed by PET imaging to obtain one or more clinically-useful images of the location and/or distribution of the [$^{18}$F]-labelled compound. In one embodiment of the present invention purification is carried out by means of a reverse-phase SPE column and/or a normal-phase SPE column, each as defined hereinabove.

The term "cleaning" in the context of the present invention refers to the process of passing a suitable amount of one or more reagents through a component to be cleaned in order to render it suitable for use in preparation of a subsequent batch of [$^{18}$F]-labelled PET tracer. In one embodiment, the cleaning step in the context of the method of the present invention comprises rinsing the reaction vessel and SPE columns with water. In another embodiment of the method of the present invention said cleaning step comprises rinsing the SPE column with acetonitrile prior to rinsing with water. In another embodiment of the method of the present invention said cleaning step comprises rinsing said SPE columns (11, 12) with ethanol prior to rinsing with water.

In one embodiment of the method of the present invention the steps are carried out in sequence.

An illustrative example of the present invention is the synthesis of [$^{18}$F]FDG on the FASTlab™ (GE Healthcare). The first [$^{18}$F]FDG synthesis is similar to the current [$^{18}$F] FDG process on FASTlab™, it uses the same amount of reagents. At the end of the first [$^{18}$F]FDG process, the first batch is sent to a first product collection vial. At this stage there is enough residual reagents in the different vials for a second [$^{18}$F]FDG synthesis. The FASTlab™ stays in waiting mode after the delivery of the first [$^{18}$F]FDG batch. From this moment the FASTlab™ is ready to receive the radioactivity from the cyclotron for a second [$^{18}$F]FDG synthesis. Once the [$^{18}$F]fluoride solution from the cyclotron is arrives in the conical vial of the cassette, the operator can start the second [$^{18}$F]FDG process, which starts with the cleaning of the tC18 column with 1 ml of acetonitrile and the rinsing with water for injection of the purification columns. The reaction vessel has already been washed during the first synthesis. A second QMA column and tubing is added to the cassette to ensure a proper trapping and elution of the [$^{18}$F]fluoride, prior to the drying step. After the elution of the [$^{18}$F]fluoride into the reactor, the rest of the [$^{18}$F]FDG process is performed the same way that the first [$^{18}$F]FDG synthesis. A separate outlet line is used. The cassette allows the two [$^{18}$F]FDG bulks to have their own outlet lines, sterilization filters and product collection vials, so the separation of the batch is clear.

Figure 3:
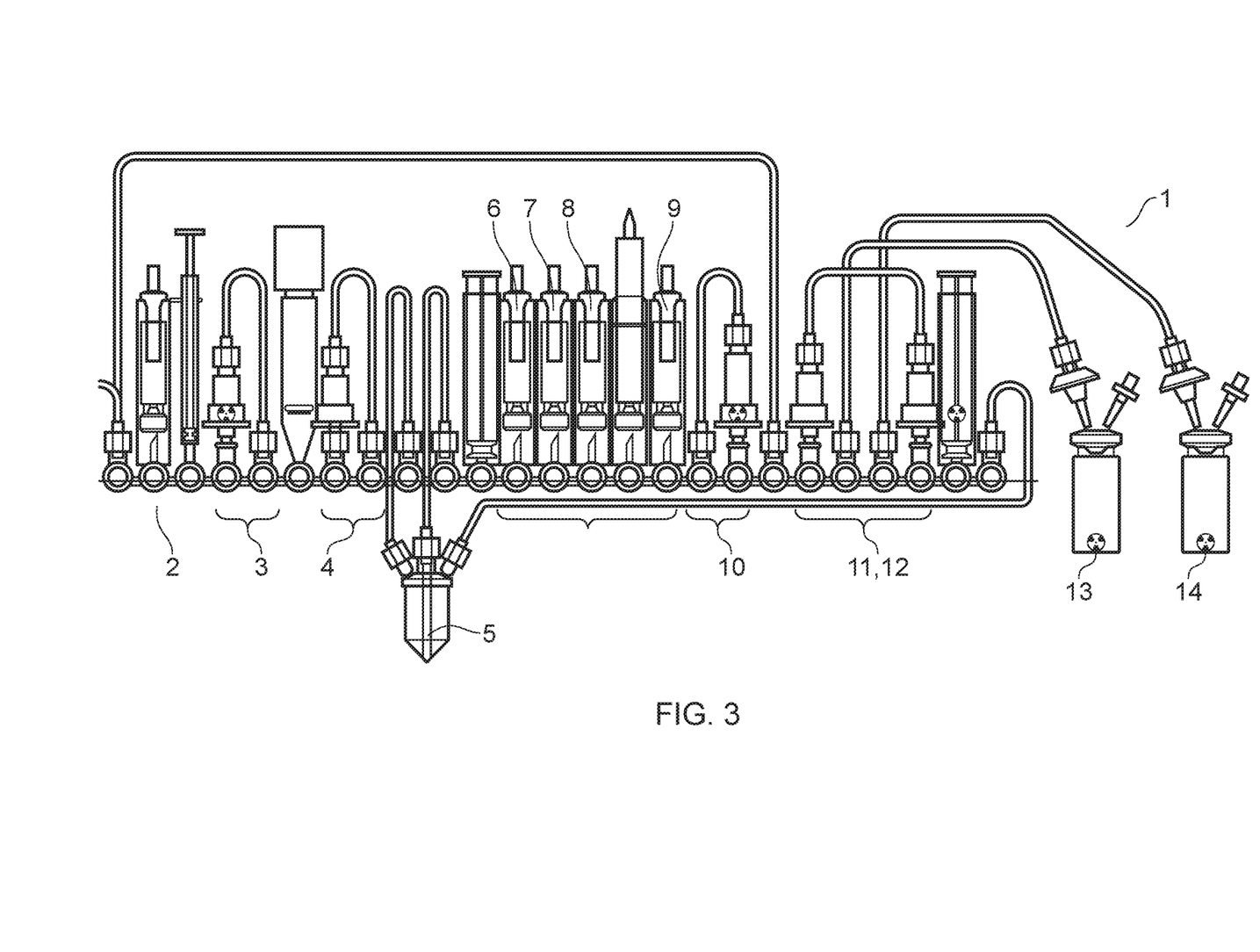
FIG. 3 illustrates a cassette suitable for carrying out two [$^{18}$F]FDG runs on FASTlab™.

FIG. 3 is a schematic drawing of a non-limiting example of a cassette of the present invention designed for the radiosynthesis of 2 consecutive batches of [$^{18}$F]FDG.

BRIEF DESCRIPTION OF THE EXAMPLES

Example 1 describes the synthesis of two batches of [$^{18}$F]FDG on one FASTlab™ cassette.

LIST OF ABBREVIATIONS USED IN THE EXAMPLES

[18F]FDG [$^{18}$F]fluorodeoxyglucose
[$^{18}$F]FTAG [$^{18}$F]fluorotetraacetylglucose
GC gas chromatography
HLB hydrophilic-lipophilic balance
IC ion chromatography
K222 4,7,13,16,21,24-Hexaoxa-1,10-diazabicyclo[8.8.8] hexacosane
MeCN acetonitrile
min minute(s)
NCY uncorrected yield
ppm parts per million
QMA quaternary methylammonium
SPE solid-phase extraction

EXAMPLES

Example 1

Synthesis of Two Batches of [$^{18}$F]FDG on One FASTlab™ Cassette

The cassette configuration as illustrated in FIG. 3 was used to produce two consecutive batches of [$^{18}$F]FDG using the following method (numbers in this method are reference numbers in FIG. 3 unless stated as a "position", which is one of positions 1-25 going from left to right on the cassette of FIG. 3):

(i) 800 µL MeCN (from vial 7) was used to condition the tC18 environmental SPE column (10), and 5 mL H$_2$O was used to condition each of the HLB SPE column (11) and the Alumina SPE column (12).

(ii) [$^{18}$F]Fluoride was obtained from the bombardment of [$^{18}$O]—H$_2$O with a high-energy proton beam extracted from a Cyclotron Cyclone 18/9 (IBA) and transferred to the cassette via the conical reservoir at position 6.

(iii) [$^{18}$F]Fluoride was trapped on the QMA column (3) and separated from the enriched water which was collected in an external vial via a pathway through positions 5-4-1.

(iv) Eluent (from vial 2) was withdrawn in the syringe at position 3 and passed through the QMA column (3) to release [$^{18}$F]fluoride and send to the reaction vessel (5).

(v) Evaporation of the water in the reaction vessel (5) was catalysed by adding a little quantity of 25 mg/mL mannose triflate precursor (vial 6 at position 12 at 120° C.

(vi) Mannose triflate precursor (from vial 6) was withdrawn in the syringe at position 11 and transferred to the reaction vessel (5) in position 10 where the labelling reaction was carried out at 125° C. for 2 minutes.

(vii) The resulting radiolabelling intermediate, [$^{18}$F]FTAG, was trapped and so, separated from unreacted fluorides, on the upper side of the tC18 environmental column (10) at position 18.

(viii) Sodium hydroxide (from vial 8) was passed through the column (10) to convert the [$^{18}$F]FTAG to [$^{18}$F]FDG collected by the syringe at position 24.

(ix) Neutralization of the resulting basic solution was carried out using phosphoric acid (from vial 9).

(x) The final product was sent to a first external collection vial (13) connected in position 21 via the two purification columns (11, 12) in a row (i.e. HLB in position 23 and Alumina in position 20).

(xi) The tC18 environmental was washed with acetonitrile from position 13 (vial 7), and the reactor, purification columns and tubing were rinsed with water from the water bag connected at the spike at position 15.

(xii) A second batch of [$^{18}$F]fluoride from the cyclotron was transferred to the cassette as in step (ii).

(xiii) The [$^{18}$F]fluoride was trapped on a new QMA column (4) found at position 8 and separated from the enriched water which is collected in an external vial via a pathway through positions 7-8-19-1.

(xiv) With [$^{18}$F]fluoride from the QMA (4) at position 8, steps (iv)-(ix) were carried out as for the first batch.

(xv) The second batch of [$^{18}$F]FDG was purified via the same columns (11, 12) in position 23 (HLB) and 20 (Alumina) and then transferred to a new external collection vial (14) connected by the tubing in position 22.

Figure 4:
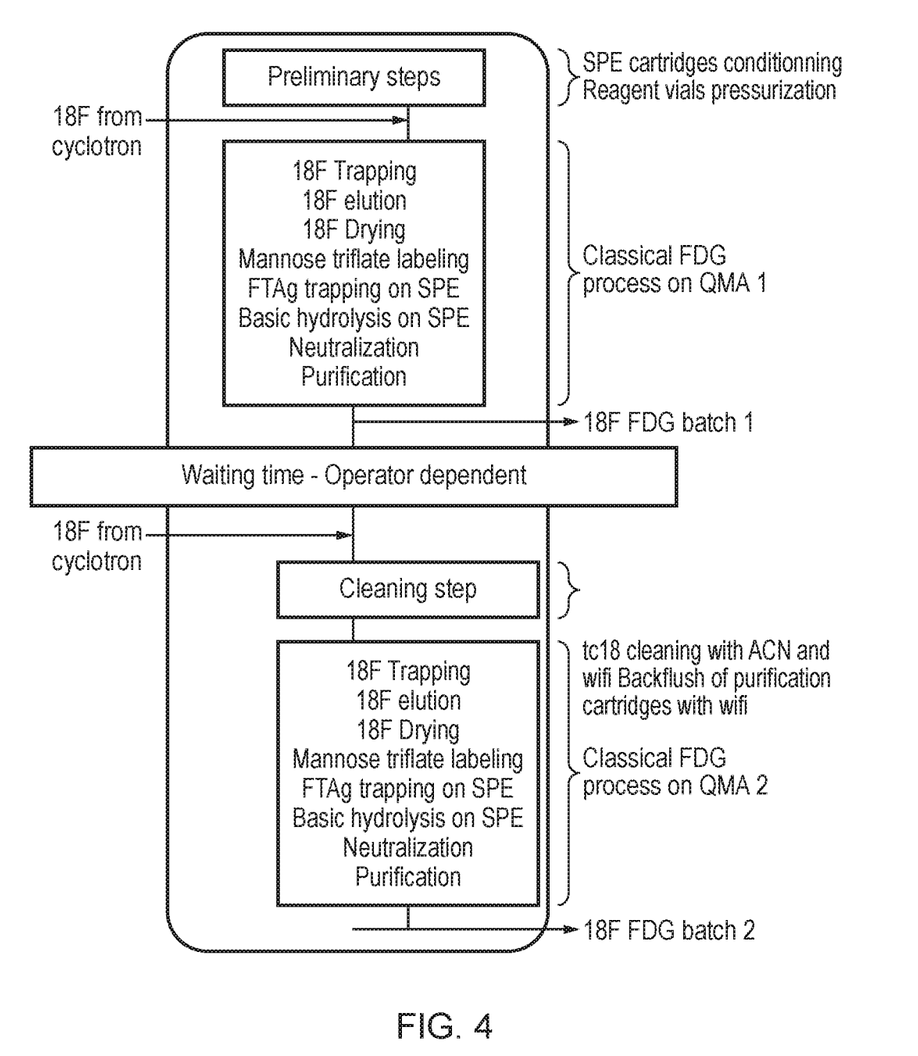
FIG. 4 illustrates the workflow for producing two [$^{18}$F] FDG batches on FASTlab™ using a single cassette such as that illustrated in FIG. 3.

This cassette configuration has an enriched water recycling pathway on the left side for the first batch (FIG. 4 top) and on the right side for the second batch (FIG. 4 bottom) of the cassette (contamination of the manifold with enriched water possible) with seven positions on the cassette engaged, i.e. position 6 for the activity inlet, position 1 with the connection of enriched water vial, position 4 for the QMA 1, position 5 for tubing of QMA 1, position 7 for QMA 2 position 8 for tubing of QMA 2 and position 19 for recovery of enriched water from batch 2.

Starting activity, final activity and residual activities were measured by a calibrated ionization chamber VEENSTRA (VIK-202).

To determine yield, the following yield Calculations were made:
if delta Tf=elapsed time after time at starting of the synthesis in min
if Af=final activity in mCi
cAf=corrected final activity in mCi regarding to starting of the synthesis in min=Af. Exp(ln(2)*(delta Tf/110)) where 110=half-life of [$^{18}$F]fluorine in minutes
if cAi=corrected starting activity in mCi regarding to starting of the synthesis in mCi
if delta Ts=duration of the synthesis
Corrected yield (CY)=(cAf/cAi)*100
Uncorrected yield (NCY)=CY*Exp(ln(2)*(–delta Ts/110))

The results below relating to starting activity, final activity and residual activities were obtained with this cassette configuration:

| Run # | Starting activity (mCi) | Non-corrected Yield (%) | Residual activity on QMA (%) | Residual activity in [$^{18}$O]-water vial (%) |
|---|---|---|---|---|
| 1a | 7,845 | 66.59 | 0.12 | 0.31 |
| 1b | 8,936 | 72.48 | 0.35 | 0.37 |
| 2a | 7,630 | 68.80 | 0.15 | 0.10 |
| 2b | 7,678 | 73.98 | 0.13 | 0.18 |
| 3a | 7,980 | 69.86 | 0.05 | 0.12 |
| 3b | 8,007 | 70.54 | 0.41 | 0.07 |

For quality control, measurements of pH, glucose concentration, acetic acid concentration and K222 concentration were made.

pH was measured using a Metrohm 744 pH meter.

Glucose concentration was determined by ion chromatography (IC) where the analytical conditions were:
Dionex IC System
Column Dionex Carbopak PA10, 4.0*250 mm @ 25° C.
Solvent KOH 100 mM @ 1 mL/min
Electrochemical detector @ 30° C.
The composition of the standard for FDG used was:
Glucose=25 μg/mL
FDM=50 μg/mL
FDG=50 μg/mL
CIDG=50 μg/mL The determination of acetic acid amount was evaluated using gas chromatography (GC) carried out on a Varian CP-3800 equipped with a CP-8400 autosampler and the following parameters:
Column: Macherey-Nagel Optima® 624-LB column, 30 m*0.32 mm ID, 1.80 μm film
Injection: volume 1 μL, split ratio 1:10, injector at 250° C.
Carrier gas: Helium 10 PSI 5 mL/min
Temperature: 80° C. from 0 to 3 min, 80 to 200° C. from 3 to 9 min at 20° C./min and finally 200° C. from 9 to 10 min.
Detector: FID at 250° C. (He 20 mL/min, H2 30 mL/min and Compressed air 260 mL/min)
Reference used: Acetic acid solution at 500 ppm w/w (which corresponds to a tenth of the limit, 5000 ppm).

The amount of K222 in the final product was determined by spotting the sample on a TLC plate which is impregnated by a revealing solution of iodoplatinate (0.5 g of Chloroplatinic acid hexa-hydrated: $H_2PtCl_6.6H_2O$ (!highly hygroscopic!), 9 g of potassium iodide: KI, 200 mL of distilled water) and comparing this with standard solutions of K222 1, 5, 10, 50 and 100 ppm). Colour intensity of the obtained stains is proportional to the amount of K222 present in the solution.

The results below were obtained:

| Run # | pH | Glucose (μg/ml) | Acetic Acid (ppm) | K222 (ppm) |
|---|---|---|---|---|
| 3a | 6.3 | 324.48 | 917 | 1 |
| 3b | 6.1 | 352.60 | 1081 | 10 |
| 4a | 6.1 | — | 1187 | 1 |
| 4b | 5.4 | — | 863 | 15 |

The invention claimed is:

1. A cassette for the synthesis of a plurality of batches of an [$^{18}$F]-labelled positron-emission tomography (PET) tracer wherein said cassette comprises:
   (i) a first anion exchange column for a first batch and a second anion exchange column for a second batch;
   (ii) a reaction vessel;
   (iii) a vial containing an aliquot of eluent for each of the batches;
   (iv) a vial containing an aliquot of a precursor compound for each of the batches;
   (v) reagent vials wherein each reagent vial contains an aliquot of reagent for each of the batches;
   (vi) a reverse phase solid-phase extraction (SPE) column for deprotection and/or one or more normal phase SPE columns for purification; and,
   (vii) means for cleaning said reaction vessel and said SPE columns, wherein the first anion exchange column, second anion exchange column, reaction vessel, vial containing an aliquot of eluent, vial containing an aliquot of precursor, reagent vials, reverse phase SPE column, one or more normal phase SPE columns, and means for cleaning are connected along a linear common pathway within the cassette.

2. The cassette as defined in claim 1 wherein said PET tracer is selected from [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F]fluorocyclobutane-1-carboxylic acid ([$^{18}$F]FACBC), [$^{18}$F]flumanezil ([$^{18}$F]FMZ), [$^{18}$F]tyrosine, [$^{18}$F]altanaserine, 4-[$^{18}$F]fluoro-3-iodobenzyl guanidine ([$^{18}$F]FIBG), meta-[$^{18}$F]fluorobenzylguanidine ([$^{18}$F]mFBG) and [$^{18}$F]5-fluorouracil.

3. The cassette as defined in claim 1 wherein said first anion exchange column and second anion exchange column are a quaternary ammonium anion exchange (QMA) columns.

4. The cassette as defined in claim 1 wherein said eluent comprises a cationic counterion dissolved in an organic-aqueous solution.

5. The cassette as defined in claim 1 wherein said means for cleaning said reaction vessel and said SPE columns comprises a source of water fluidly connected to said reaction vessel and to said SPE columns.

6. The cassette as defined in claim 5 wherein said means for cleaning said reaction vessel and said SPE columns comprises a source of acetonitrile fluidly connected to said SPE column for deprotection.

7. The cassette as defined in claim 6 wherein said means for cleaning said reaction vessel and said SPE columns comprises a source of ethanol fluidly connected to said SPE columns for purification.

8. A method for the synthesis of a plurality of batches of an [$^{18}$F]-labelled PET tracer in a cassette wherein said method comprises:

(a) trapping a first aliquot of [$^{18}$F]fluoride onto a first anion exchange column;

(b) providing a first aliquot of a precursor compound in a reaction vessel;

(c) passing a first aliquot of eluent through said first anion exchange column to elute said first aliquot of [$^{18}$F] fluoride into said reaction vessel;

(d) heating the reaction vessel for a predetermined time to obtain crude [$^{18}$F]-labelled PET tracer;

(e) deprotecting said crude [$^{18}$F]-labelled PET tracer on a reverse phase SPE column;

(f) purifying said crude [$^{18}$F]-labelled PET tracer on one or more normal phase SPE columns;

(g) cleaning said reaction vessel and said SPE columns;

(h) repeating steps (a)-(g) at least once, using a second aliquot of [$^{18}$F]fluoride, a second anion exchange column and a second aliquot of a precursor compound;

wherein the first anion exchange column, reaction vessel, vial containing an aliquot of eluent, vial containing an aliquot of precursor, reagent vial, reverse phase SPE column, the one or more normal phase SPE columns are connected along a linear common pathway within the cassette.

9. The method as defined in claim 8 wherein said PET tracer is selected from [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F] fluorocyclobutane-1-carboxylic acid ([$^{18}$F]FACBC), [$^{18}$F] flumanezil ([$^{18}$F] FMZ), [$^{18}$F]tyrosine, [$^{18}$F]altanasaltanase, 4-[$^{18}$F]fluoro-3-iodobenzyl guanidine ([$^{18}$F]FIBG), meta-[$^{18}$F]fluorobenzylguanidine ([$^{18}$F]mFBG) and [$^{18}$F]5-fluorouracil.

10. The method as defined in claim 9 wherein each of said first anion exchange column and said second anion exchange column is a quaternary ammonium anion exchange (QMA) column.

11. The method as defined in any one of claim 10 wherein said eluent comprises a cationic counterion dissolved in an organic-aqueous solution.

12. The method as defined in claim 11 wherein said cleaning step comprises rinsing said reaction vessel and said SPE columns with water.

13. The method as defined in claim 12 wherein said cleaning step comprises rinsing said SPE columns with acetonitrile prior to rinsing with water.

14. The method as defined in claim 13 wherein said cleaning step comprises rinsing said SPE columns with ethanol prior to rinsing with water.

\* \* \* \* \*